United States Patent
Mitoma

[19]

[11] Patent Number: 6,144,448
[45] Date of Patent: Nov. 7, 2000

[54] FLUORESCENCE DETECTING APPARATUS

[75] Inventor: Yasutami Mitoma, Kanagawa-ken, Japan

[73] Assignee: Tosoh Corporation, Yamaguchi-ken, Japan

[21] Appl. No.: 09/517,666

[22] Filed: Oct. 30, 1996

Related U.S. Application Data

[63] Continuation of application No. 08/087,855, Jul. 9, 1993, abandoned.

[30] Foreign Application Priority Data

Jul. 17, 1992 [JP] Japan .................................. 4-212288

[51] Int. Cl.$^7$ .................................................. G01N 21/64
[52] U.S. Cl. ...................... 356/317; 250/458.1; 435/808; 436/172
[58] Field of Search .................................... 356/317, 318, 356/417, 440; 250/458.1, 459.1, 461.1, 461.2; 435/34, 289–291, 808; 422/82.07–82.08, 82.11; 436/172

[56] References Cited

U.S. PATENT DOCUMENTS

| | | | |
|---|---|---|---|
| 3,992,631 | 11/1976 | Harte . | |
| 4,498,780 | 2/1985 | Banno et al. ........................ | 356/440 X |
| 5,217,876 | 6/1993 | Turner et al. .............................. | 435/34 |
| 5,252,834 | 10/1993 | Lin ....................................... | 250/458.1 |
| 5,371,016 | 12/1994 | Berndt .................................... | 356/461.2 |
| 5,473,437 | 12/1995 | Blumenfeld et al. .................... | 356/417 |

FOREIGN PATENT DOCUMENTS

| | | |
|---|---|---|
| 0 127 286 | 12/1984 | European Pat. Off. . |
| 0 127 418 | 12/1984 | European Pat. Off. . |
| 0 266 881 | 5/1988 | European Pat. Off. . |
| 0 156 274 A2 | 12/1992 | European Pat. Off. . |
| WO 87/06716 | 11/1987 | WIPO . |

OTHER PUBLICATIONS

Bio/Technology vol. 10 Apr. 1992 Research pp. 413–417 Higuchi et al Simultaneous Amplification and Detection of Specific DNA Sequences.

*Primary Examiner*—F. L. Evans
*Attorney, Agent, or Firm*—Nixon & Vanderhye

[57] ABSTRACT

A fluorescence detecting apparatus which allows highly precise measurement of fluorescence even with minute sample amounts, which has a strong responsiveness to temperature variations, which allows simultaneous measurement of a plurality of samples, and wherein the light source and the container holder, and the container holder and the fluorescence detector, are each optically connected by optical fibers; and the optical fibers are connected to the container holder in such a manner that the sample in the container is excited for fluorescence from below the sample container held by the container holder, and that they may receive the fluorescent light which is emitted by the sample from below the sample container.

13 Claims, 4 Drawing Sheets

FLUORESCENCE DETECTING APPARATUS

This is a continuation of application Ser. No. 08/087,855, filed Jul. 9, 1993, now abandoned.

FIELD OF THE INVENTION

The present invention relates to a fluorescence detecting apparatus, and more specifically, it relates to a fluorescence detecting apparatus for measuring variations in the fluorescent properties of substances or their interacted complexes in reactions which occur between at least two types of substances capable of interaction between each other, for example, reactions involving nucleic acids and intercalatory fluorescent pigments, lipid bilayers and hydrophobic fluorescent probes, proteins and fluorescent pigments, organic polymers and fluorescent pigments, etc.

DESCRIPTION OF THE PRIOR ART

In reactions which occur between at least two types of substances capable of interaction between each other, for example, reactions involving nucleic acids and intercalatory fluorescent pigments, lipid bilayers and hydrophobic fluorescent probes, proteins and fluorescent pigments, organic polymers and fluorescent pigments, etc., the fluorescent properties of these substances or their interacted complexes vary depending upon their state. Thus, if the variation in the fluorescent properties thereof is measured, it is possible to know the state of interreaction of the above substances, the amount of complex formed, etc.

In polymerase chain reactions (PCRs) which are conducted in the copresence of an intercalatory fluorescent pigment (for example Japanese Patent Application Hei 3-313616) etc., it is possible to know the state of nucleic acid amplification (success of the PCR) by measuring the fluorescent properties at a desired point in each cycle of the PCR, and usually at a point during repetition of separation of the double-stranded nucleic acid into single strands and hybridization between single strands, by variation of the temperature. In this procedure, a device is required which can vary the temperature according to a preset program and measure the change in the fluorescent properties of a sample in a sample container. Such a device in current use is a spectrophotometer containing a temperature-controlling cell holder.

SUMMARY OF THE INVENTION

Measurement of fluorescent property variation according to the prior art using a spectrophotometer employs a system in which exciting light is directed towards a cell using an optical system of lenses, mirrors, etc., and fluorescence is directed towards a fluorescence detecting apparatus in the same manner, and therefore it has been difficult to effect multichannel measurement (simultaneous measurement of multiple samples). Furthermore, the responsiveness of the sample temperature to the temperature variation is lessened by the amount of liquid in the sample, and it is difficult to measure the rapid interactions between compounds which accompany phase transitions.

Various attempts have been made at improving temperature responsiveness, but in methods where the volume of the sample container is reduced, etc. it becomes necessary to select the beam of the exciting light, thus causing new problems such as a reduction in the quantity of light and a resulting decrease in the precision of measurement. An attempt at improvement has been made by using an intense light source to compensate for the reduction in the quantity of light, but in this case the problem of heat waste from the device and the influence of heat on the fluorescence detecting apparatus are considerable, and thus it becomes difficult to obtain highly precise and repeatable measurement results.

Very recently, devices which employ optical fibers in an optical system (Biotechnology, Vol. 10, p. 413, 1992) have become known, but in these devices the sample is excited from the top of the sample container, and the fluorescence from the sample is also received from the top, and therefore if the amount of the sample is small, there is a loss of exciting light and fluorescence from the sample in the air layer between the sample and the tip of the optical fibers. The process is thus complicated by the necessity of replacing the sample container from time to time, depending on the volume of the sample, in order to overcome this problem, and therefore improvement thereof is in order.

DETAILED DESCRIPTION OF THE INVENTION

Figure 1:
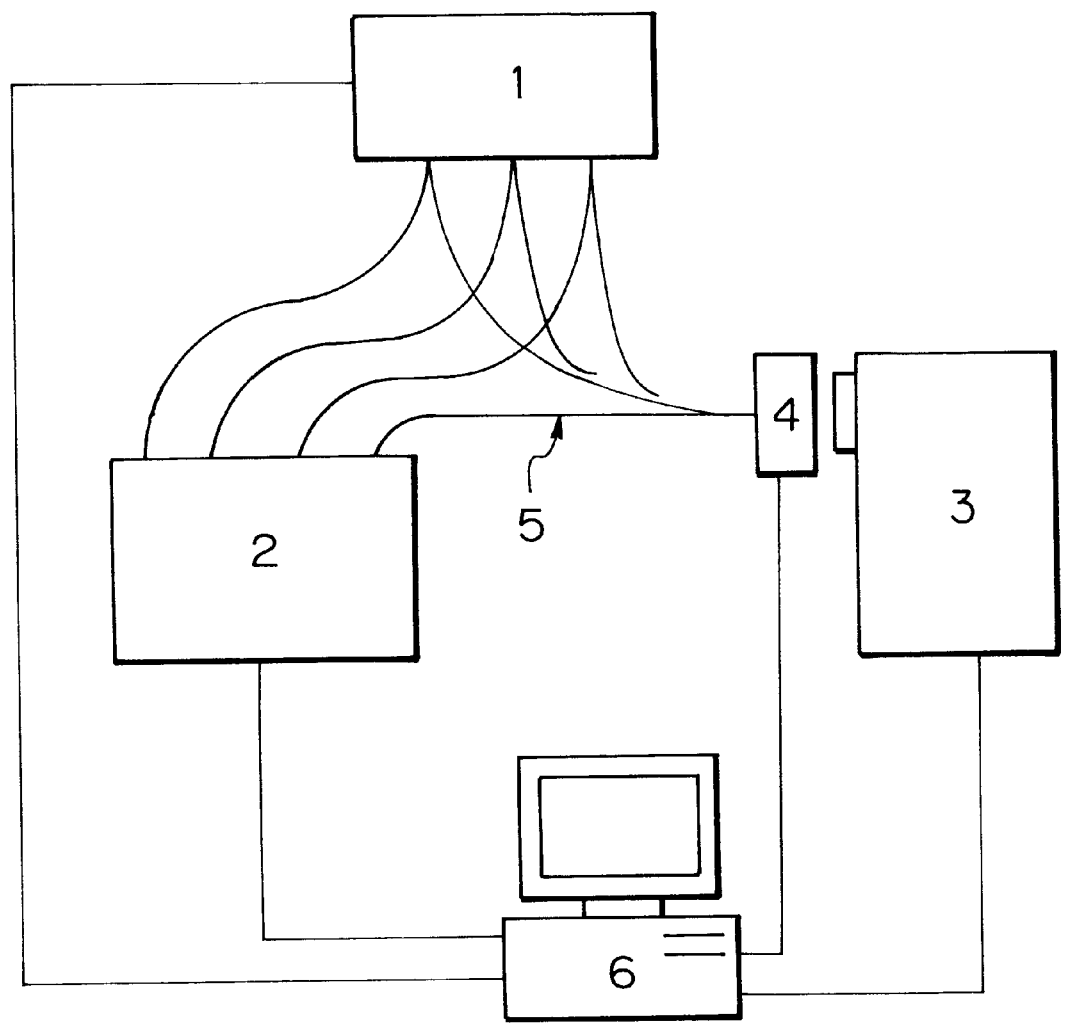
FIG. 1 is a drawing showing the construction of an apparatus according to the present invention.

The present invention relates to a fluorescence detecting apparatus which comprises a sample container which holds a sample, a container holder which holds the sample container and is capable of varying the temperature of the sample in the sample container which it holds, a fluorescence detector for measuring the fluorescence from the sample, and a light source which emits exciting light to excite the sample for fluorescence, characterized in that the light source and the container holder, and the container holder and the fluorescence detector, are each optically connected by optical fibers; and said optical fibers are connected to the container holder in such a manner that the sample in the container is excited for fluorescence from below the sample container held by the container holder, and that they may receive the fluorescent light which is emitted by the sample from below the sample container. A more detailed description of the present invention is provided below. The sample container for holding the sample may be of any shape, but in order to excite the sample from the bottom of the container and to receive fluorescence of the sample from the bottom of the container, a container is used of which at least the bottom is light-permeable. In reaction systems such as the PCR, wherein there exists the danger of infection of viral nucleic acids, etc. and the slightest contamination between two or more samples results in a large experimental error, it is preferable to use a sealable reaction container and to supply the samples to the detector under sealed conditions. An example of a sealable sample container is a commercially available centrifuge tube (for example, an Eppendorf microcentrifuge tube, etc.). Also, there is not particular restriction on the material, provided it satisfies the conditions described above.

The container holder used to hold the sample container has a function for varying the temperature of the sample, and also serves to hold the container. It may be, for example, in the form of a container holder shaped to fit the container used, or be constructed, for example, in a large box shape with said container simply being placed therein.

If the container holder is constructed in the form of a container holder shaped to fit the container, then it may be constructed so that variation in the temperature of samples may be achieved by, for example, varying the temperature of the container holder itself to vary the temperature of the sample container, thus varying the temperature of the sample in the sample container. In this case, the container holder and sample container are preferably constructed of a highly thermoconductive material. An example which may be mentioned is a heater, etc. installed on the surface of contact of the container holder with the container, in a position which does not interfere with excitement or reception of the fluorescent light. If the container holder is constructed in the form of a large box shape, then the temperature of the sample may be varied by installing a heater therein, creating a refrigerant circuit, or by air-conditioning or liquid bath, etc. In addition to these, a variety of other methods may be employed to vary the temperature of the sample according to the present invention. Since there is no need for heating when varying the temperature of the sample within a temperature range of, for example, room temperature or lower, in such cases only cooling means may be provided. Thus, the container holder is preferably constructed with attention to the desired range of variation of the sample temperature.

The fluorescence detector may be any one which is capable of measuring fluorescence from a sample. Here, "fluorescence" includes fluorescence intensity, fluorescence spectrum, etc., and these can be measured using a photomultiplier or a photodiode.

The light source to be used may be a xenon lamp, a D2 lamp, a mercury lamp, a halogen lamp, a discharge tube, laser light, or the like. According to the present invention, optical fibers are used both to direct the exciting light from the light source to the sample, and to direct the fluorescent light from the sample to the detecting apparatus. However, this does not exclude a construction wherein, for example, common optical parts such as lenses or mirrors are used near the light source in addition to the optical fibers, and the light focussed thereby is directed to the optical fibers.

Two systems of optical fibers are used, one for directing the exciting light to the sample, and the other for directing fluorescent light from the sample to the fluorescence detector. Also, by using, for example a dichroic mirror or the like, the above mentioned 2 systems may be provided for by a single optical fiber (one line). The ends of the optical fibers of each system are connected directly to the light source and the fluorescence detector, respectively, via the above mentioned optical parts or if necessary a light amplifier, etc. If the two systems are provided for by a single optical fiber line, then an auxiliary optical system is attached thereto to direct light branched at the dichroic mirror provided at one end to the light source or the detector. The other end of the optical fiber line is connected to the container holder so that exciting light is radiated to the sample from below the sample container held by the container holder, and so that fluorescence from the sample is received from below the sample container. For example, if the container holder is in the form of a holder shaped to fit the container, then the fibers may be connected so as to provide a through-opening on the concave section thereof, but in order to allow for highly precise and repeatable measurement of small amounts of samples, they are preferably connected at the deepest area of the concave section.

The end of the optical fiber line for directing the exciting light and the one for receiving the fluorescent light may each be connected separately to the container holder. For example, the ends of the exciting light radiation fibers or the fluorescent light receiving fibers may be arranged so as to intersect over an extension wire, or they may be arranged to be parallel to each other. For a more sensitive and repeatable measurement of fluorescence according to the present invention, it is preferable to construct the ends of the fibers of the two systems in proximity to each other, and it is particularly preferable to construct the ends using fibers of two coaxial systems. If the ends are constructed using fibers of two coaxial system, then it is preferable to position the ends of the fibers for receiving the fluorescent light from the sample on the exterior, and the ends of the optical fibers for directing the exciting light in the center, since this allows for reception of weaker fluorescence. As mentioned previously, if the two systems are provided for by a single optical fiber line, then the end of the fiber line may be simply connected to the container holder.

The source of the exciting light is normally selected to maximize the light intensity, but in cases where there exists the possibility of deterioration of the sample due to the radiation of the exciting light, a light-interrupting shutter may be provided to prevent the exciting light from radiating onto the sample, and the shutter may be opened and closed only at the time of measurement of the fluorescence to avoid constant bombardment of the exciting light onto the sample. The light-interrupting shutter is provided in the optical path running from the light source to the container holder, but the simplest construction is one in which a movable shutter is constructed between the ends of the optical fibers and the light source, and the shutter is mechanically or electrically moved to open and close in synchronization with the timing of measurement of the fluorescence. This timing may be, for example, the time at which the temperature of the container holder falls within a desired range (i.e., the time at which the sample in the container is thought to be in the desired range). Such a procedure is particularly effective in cases where continuous (intermittent) detection of fluorescence from two identical samples is made, such as in the fluorescence measurement in PCRs, as disclosed in Japanese Patent Application Hei 3-313616.

The variation of the temperature of the container holder for varying the sample temperature may be effected within a desired range, and this may be stored in a program, and a controller for controlling the temperature of the container holder may be attached to the apparatus according to the present invention. The controller may include a sensor for sensing the temperature of the container holder and means for storing the above mentioned program, and may compare the signal from the above mentioned sensor and the contents of the program, outputting an indication for heating or cooling of the container holder, and this purpose may be achieved by using a microcomputer or the like. If the controller functions to control the detector, light source and shutter, etc. of the present invention, then it is possible to achieve an automatic fluorescence detecting apparatus which varies the temperature of a sample when the sample container is placed in the container holder, and which can measure fluorescence by opening and closing the shutter in accordance with the timing.

The apparatus according to the present invention is suitable for use in PCRs. In this case, it is particularly preferable that the above mentioned sample container be sealed. The PCR is a reaction which amplifies the nucleic acid in a sample, and for the purpose of preventing secondary contamination a fluorescence detecting apparatus according to the present invention which employs a sealed sample container is most effective. This is because, by using a sealed container, it is possible to keep to a minimum the contamination of nucleic acids by other samples, which is a cause of false positivity in PCRs.

In most PCRs, completion is not after a single procedure. This is because the separation of double-stranded nucleic acids into single-stranded nucleic acids by varying the temperature of the sample, annealing of a primer to each of the single-stranded nucleic acids, and the extension reaction of nucleic acids originating from the primer (which results in the appearance of double-stranded nucleic acids) are conducted as one cycle, and the cycle is usually repeated. Thus, an apparatus according to the present invention which is suitable for PCRs, is preferably provided with the above mentioned shutter.

Because the above mentioned cycle is repeated, the temperature variation of the container holder is actually the variation between the temperature at which the nucleic acids can exist in double-stranded form (if the object nucleic acid is double-stranded, then this temperature range is applied at the start of the above mentioned cycle, at the time of extension of the primer, and appearance of the double-stranded nucleic acid resulting from the above mentioned extension) and the temperature at which they can only exist in single-stranded form (this temperature range is applied for division of the double-stranded nucleic acid into single strands).

With reactions involving nucleic acids and intercalatory fluorescent pigments as a case in point, here the fluorescent properties of the fluorescent pigment themselves vary in a temperature-dependent manner, and thus the timing of variation of the temperature of a sample in a PCR and opening and shutting of the above mentioned shutter is preferably such that the measurement is made at a stage wherein a fixed temperature has been reached after completion of a series of temperature variations, rather than during variation of the temperature. Furthermore, in this reaction, since a fluorescent pigment is taken up in the nucleic acid extension reaction which originates with a primer, and the fluorescent properties thereof vary, the reaction may be monitored to determine whether or not the PCR is successful (Japanese Patent Application Hei 3-313616); however, here as well the temperature range may be one in which the nucleic acids can exist in double-stranded form, and a timing which maintains a fixed temperature in the interior of the sample container is preferable. In concrete terms, this is at the moment of completion of the above mentioned cycle.

An explanation of the present invention will now be given with reference to the drawings. FIG. 1 is a drawing showing the entire body of an apparatus according to the present invention. 1 represents a container holder for holding a sample container, provided with a plurality of concave sections for holding containers to allow measurement of a plurality of samples, and optical fibers 5 on each concave section. 2 represents a fluorescence detector, 3 a light source, 4 a shutter, 5 optical fibers, and 6 a controller. FIG. 1 shows a case wherein the end surfaces of the optical fibers for irradiating exciting light and the end surfaces of the optical fibers for receiving fluorescent light are arranged coaxially. Also, in this embodiment the controller used is a microcomputer, and it controls the container holder, the fluorescence detector, the light source and the shutter.

The temperature of the container holder is varied according to the temperature variation program stored in the controller, in order to vary the temperature of the sample in the sample container (not shown). The light source is on during this time, or is controlled to be on in synchronization with the timing of measurement of the fluorescence. The controller opens and closes the shutter according to a prescribed timing, following the signal from a temperature sensor (not shown), thus exciting the sample and allowing the fluorescence to be measured by the fluorescence detector. In this apparatus, the results of measurement by the fluorescence detector may be read by the controller and later displayed.

Figure 2:
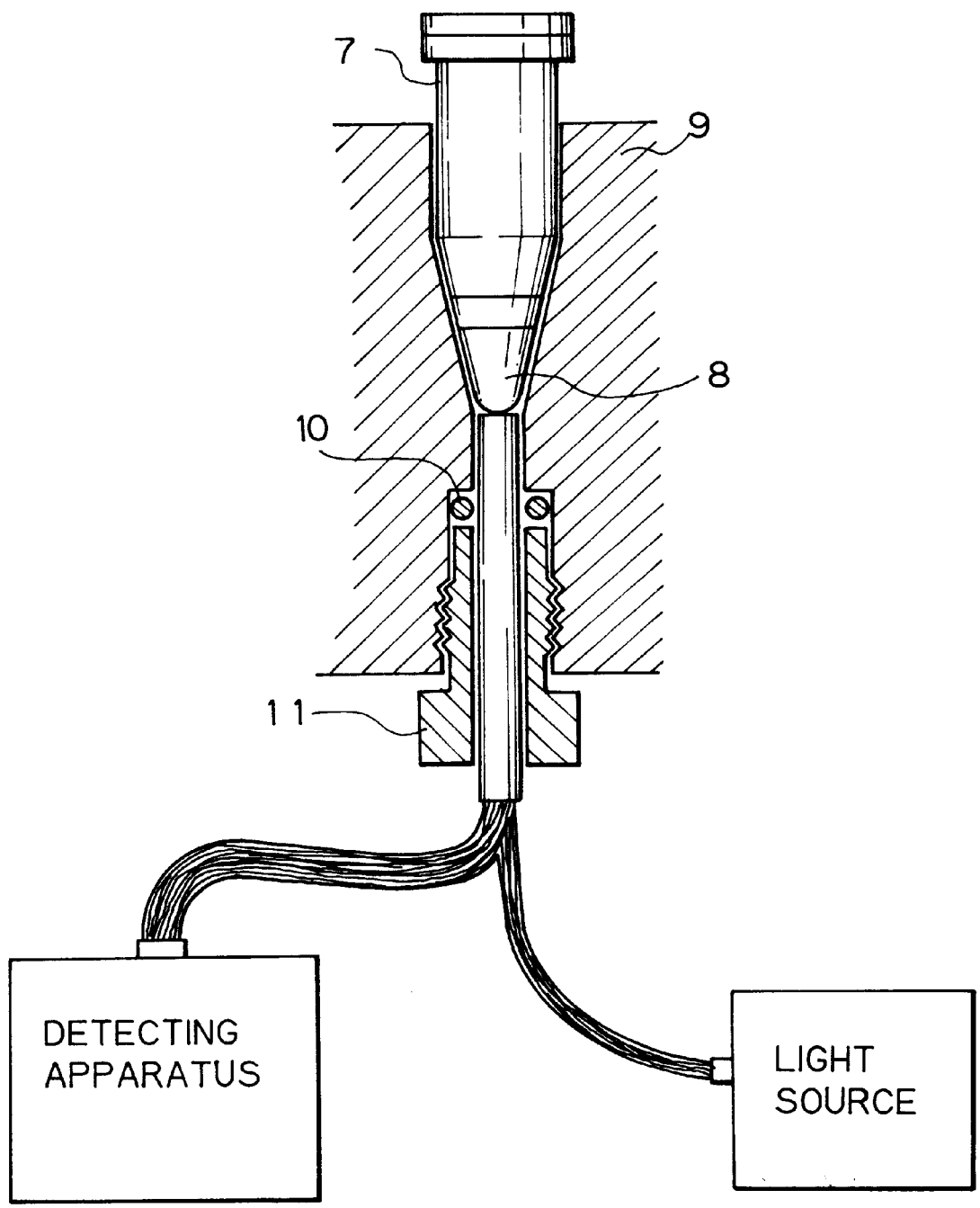
FIG. 2 is a drawing showing the periphery of the container holder of the apparatus in FIG. 1.

FIG. 2 is a drawing showing the periphery of the container holder of the apparatus explained in FIG. 1. 7 represents a sealed sample container, 8 a sample in the container, 9 an aluminum container holder which holds the sample container (only one of the plurality of concave sections in shown), 10 an O-ring and 11 a screw which connects the optical fibers to the container holder. In this embodiment, 48 fibers are bunched together and arranged around the perimeter, with 12 for irradiation of the exciting light and the remaining 36 for receiving the fluorescent light.

EXAMPLES

Examples will now be provided to illustrate the apparatus according to the present invention and measurement of fluorescence using it, without limiting the present invention thereto.

Example 1

Using a commercially available DNA synthesis kit (GeneAmp, trade name, product of Takara Brewing Co.) and the apparatus shown in FIGS. 1 and 2, amplification of nucleic acids was effected using the PCR (1 cycle= denaturation at 94° C. for 1 minute, annealing at 55° C. for 1 minute, extension at 72° C. for 1 minute (using Taq polymerase), and 30 cycles were repeated in the presence of an intercalatory fluorescent pigment (Pigment 33258, product of Hoechst AG). The reaction solution for the PCR was prepared using a calibrating $\lambda$-DNA and 1 set of primer included in the kit, and following the directions for the kit. The fluorescent pigment was added to a concentration of 1 $\mu$g/ml. The composition of the reaction solution is listed below.

| | | |
|---|---|---|
| $\lambda$-DNA (1 $\mu$g, 0.1 $\mu$g or 0.01 $\mu$g/ml) | | 10 $\mu$l |
| 10 × reaction buffer solution | | 10 $\mu$l |
| (Sodium chloride | | 0.5 M) |
| (Tris-HCl buffer solution (pH 8.0) | | 0.1 M) |
| (Magnesium chloride | | 15 mM) |
| (Gelatin (weight/volume) | | 0.01%) |
| Intercalatory fluorescent pigment (final concentration) | | 1 ug/ml |
| Primer 1 and Primer 2 | (20 $\mu$M) | 1 $\mu$l ea |
| (Primer 1: | $\lambda$-DNA, corresponding to 7131-7155, anti sense strand GATGAGTTCGTGTCCGTACAACTGG) | |

-continued

| (Primer 2: | λ-DNA, corresponding to 7607-7630, sense strand GGTTATCGAAATCAGCCACAGCGCC) | |
|---|---|---|
| dNTP mixture | (2.5 mM ea) | 8 μl |
| Water | | 59.5 μl |
| Taq polymerase | (5 units/μl) | 0.5 μl |

In the apparatus shown in FIGS. 1 and 2, optical fibers (Superesca, product of Mitsubishi Rayon), a controller (DCP200, product of Yamatake Honeywell) and a light source (50 W xenon lamp; light power source: Model C-2576, both products of Hamamatsu Photonics) were used, and the shutter and fluorescence detector were manufactured in-house.

For the three different samples prepared in the above manner having different initial λ-DNA concentrations, 25 μl of each reaction solution was sampled in a microcentrifuge tube (product of Biobic), mineral oil was superpositioned on the surface thereof to prevent evaporation of the sample, which was carried on an aluminum block, and the PCR was carried out while raising and lowering the temperature. Exciting light from the xenon lamp light source and passing through a U350 color glass filter was focussed with a lens, directed towards the optical fibers, and irradiated from the bottom of the sample container to the sample. The fluorescence from the sample was received by the optical fibers at the bottom of the reaction container, and the light which passed through a 400–450 nm interference filter was measured with the in-house manufactured fluorescence detector which contained a photodiode. The measurement of the fluorescence was made during the final second of the extension reaction of the above mentioned reaction cycle.

Figure 3:
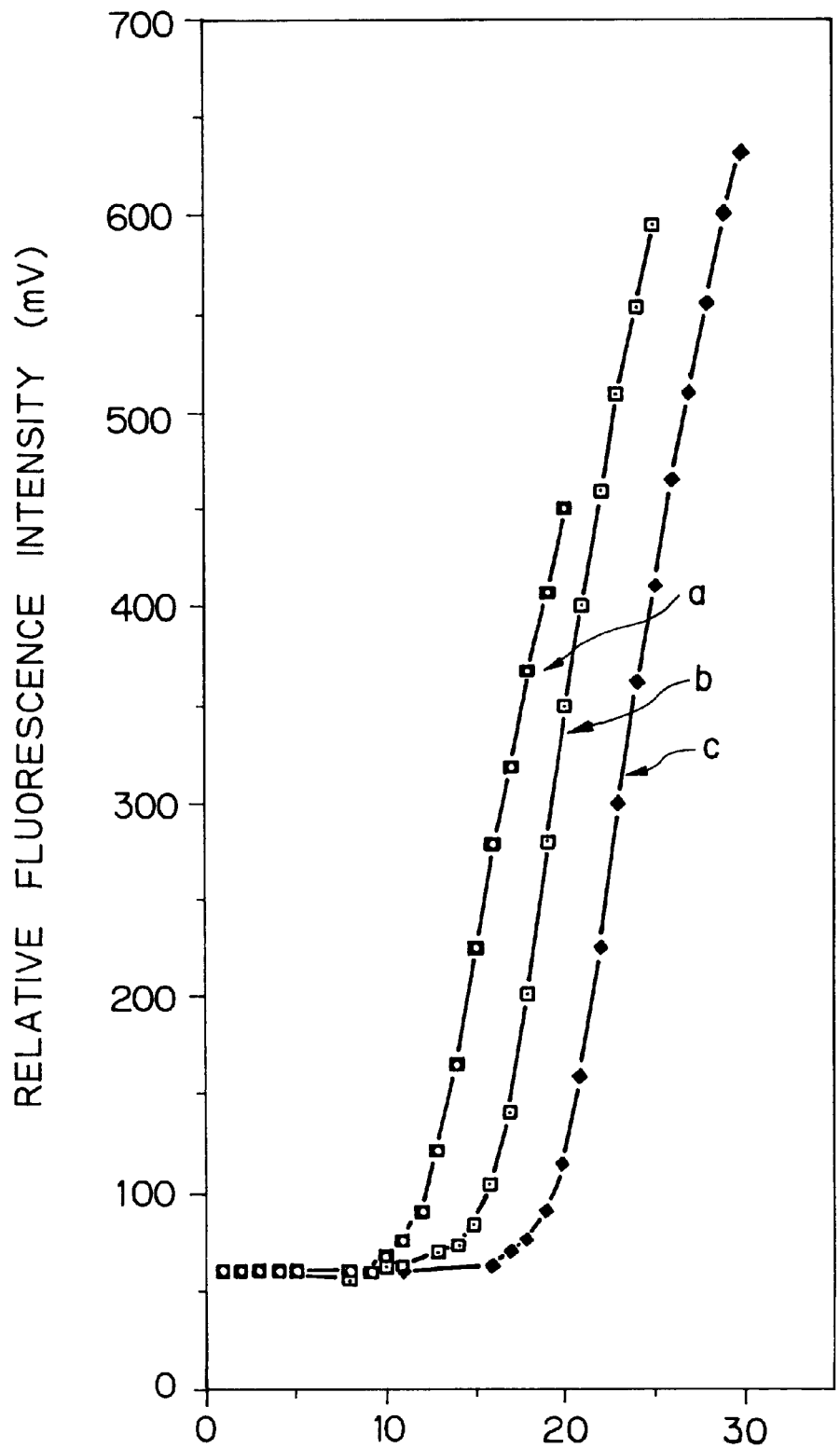
FIG. 3 is a graph showing the results of Example 1, with the fluorescence intensity during the PCR cycle for various concentrations of $\lambda$DNA plotted on the vertical axis, and the number of PCR cycles plotted on the horizontal axis. In the figure, "a" represents a case where the amount of DNA is 2.5 ng, "b" a case where it is 0.25 ng, and "c" a case where it is 0.025 ng.

The resulting measurement of the variation in fluorescence during the PCR was as shown in FIG. 3. In FIG. 3, the fluorescence intensity during the PCR cycle for each concentration of λ-DNA is plotted on the vertical axis, and the number of cycles is plotted on the horizontal axis, and it is clear from this graph that the number of cycles required for an increase in the fluorescence intensity depended on the concentration of the sample; that is, 3 curves were obtained with different increase points depending on the initial amount of DNA in the sample.

Example 2

Using the amplified sample from Example 1, continuous measurement was made of the fluorescence intensity at temperatures (94, 72, 55° C.) predetermined for the double-stranded nucleic acid fragments (approximately 500 base pairs) and during a state of continuous variation of the temperature to each one, in the presence of an intercalatory fluorescent pigment.

Figure 4:
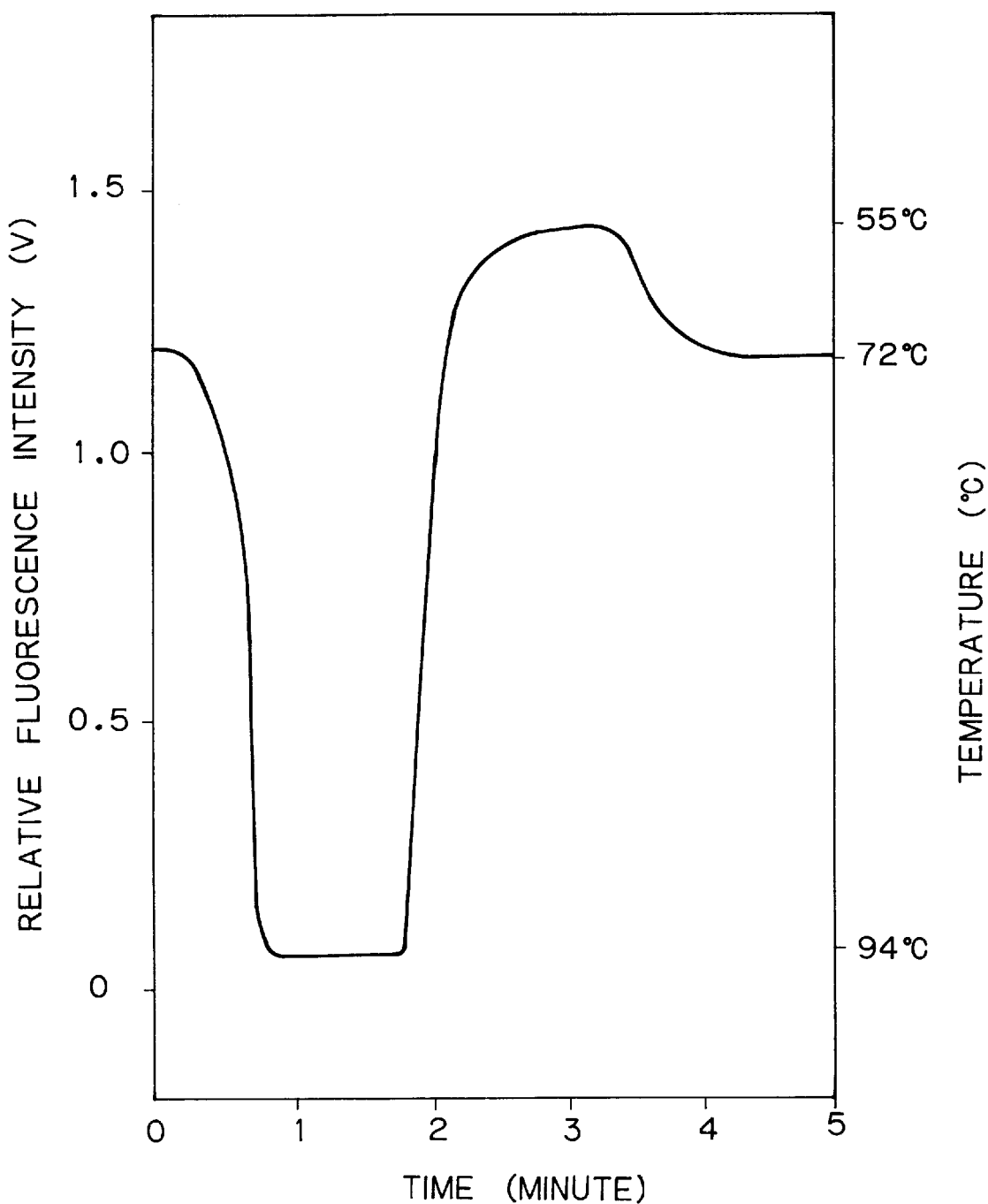
FIG. 4 is a graph showing the results of Example 2, with the fluorescence intensity during a PCR conducted in the presence of an intercalatory fluorescent pigment plotted on the vertical axis, indicating temperatures of the sample at the time of measurement of the fluorescence intensity on the right-hand side, and the time plotted on the horizontal axis.

The resulting measurement of the variation in fluorescence was as shown in FIG. 4. In FIG. 4, the time is plotted on the horizontal axis, and the fluorescence intensity on the vertical axis.

Example 3

Of λ-DNA which had been digested with EcoT14I, 1 μg was suspended in 25 μl of a buffer solution (50 mM of NaCl, 1 μg/ml of intercalatory fluorescent pigment (33258, product of Hoechst AG), 10 mM of Tris-HCl, pH 8.5), the suspension was placed in a 25 ul microcentrifuge tube (product of Biobic), and the fluorescence intensity was measured using an apparatus similar to the one in Example 2, except that coaxial fibers (E32-CC200, product of Omron) were used. For comparison, the above mentioned optical fibers were affixed to the upper opening of the microcentrifuge tube for measurement in the same manner. For this purpose, the end surfaces of the optical fibers positioned at the liquid surface of the sample in the centrifuge tube and at the above mentioned opening were separated by a gap of 23 mm.

The above mentioned optical fibers consisted of one 1 mm diameter fiber in the center, and 16 lines of 0.25 mm fibers around the periphery, with the center fiber used for irradiating exciting light, and the peripheral fibers used for receiving fluorescent light. In this embodiment, a 50 W xenon lamp is used as the light source, and measurement was made of the exciting light which was transmitted through a U-350 filter and of the fluorescent light which was transmitted through an interference filter (400–450 nm).

As a result, a fluorescence intensity of 265 mV was obtained with the apparatus according to the present invention, whereas the fluorescence intensity from the same sample was measured to be 20 mV, or only about $\frac{1}{13}$ in comparison, when the optical fibers were attached to the upper opening of the centrifuge tube.

EFFECT OF THE INVENTION

According to the present invention, since the light source, the container holder (i.e., the sample) and the fluorescence detector are all connected by the optical fibers, it is possible to arrange all of these separately so that the heat-emitting light source and the container holder do not affect the fluorescence detector. Furthermore, multichannel measurement, or direction of exciting light from a single light source to a plurality of samples, and direction of fluorescence from a plurality of samples to a detector, may be easily realized. If highly photoconductive fibers are used, then the loss of the exciting light and fluorescent light may be prevented and the light beam may be selected, and therefore it is possible to make high precision measurements even in the case of, for example, minute sample amounts, etc.

According to the present invention, exciting light is irradiated onto the bottom of a sample container, and fluorescent light is received at the bottom of the sample, and therefore the air layer between samples may be kept to a minimum. As a result, highly precise measurements are possible particularly in cases where fluorescence is measured from minute sample amounts.

The significance of using minute sample amounts is that the responsiveness of samples to temperature variation may be improved, and therefore that in reactions involving substances which undergo temperature-dependent phase transitions and have been difficult to measure according to the prior art . . . for example, reactions involving intercalatory fluorescent pigments and nucleic acids, reactions involving lipid bilayers and hydrophobic fluorescent probes, reactions involving proteins and fluorescent pigments, and reactions involving organic polymers and fluorescent pigments . . . the measurement of rapid interactions between compounds which result from phase interactions due to temperature variations may be made by measuring the variation in the fluorescent properties thereof.

Particularly, if an apparatus according to the present invention is used in a PCR in which an intercalatory pigment is added, and the fluorescence intensity is measured according to a desired timing during each cycle, or the variation in the fluorescence is measured throughout each cycle, then it is possible to know the progress of nucleic acid amplification, i.e., the success of the PCR, from these measurements. Therefore, according to the present invention it is also easily possible to know the success of PCRs, which has conventionally been determined by electrophoresis, etc. This means that waste may be reduced in cases where the initial concentration of the object nucleic acid is high and the PCR continues unnoticed even after saturation of the amplification reaction, resulting in the amplification of non-specific nucleic acids, and further means that the subsequent process of identification of the nucleic acids may be facilitated. If the fluorescent property at an appropriate wavelength for the PCR is measured and a sealed sample container is used, then there is no need to remove the sample from the container for measurement, and this is very effective in avoiding false positivity, particularly in the case of samples with a high probability of secondary contamination, etc.

What is claimed is:

1. A fluorescence detecting apparatus comprising:
   a sealed sample container for holding a sample;
   a container holder for holding the sample container and means for varying the temperature of the sample in the sample container;
   a fluorescence detector for measuring the fluorescence from the sample; and
   a light source for emitting an exciting light to excite the sample for fluorescence;
   wherein said light source and said container holder, and said container holder and said fluorescence detector, are each optically connected by optical fibers;
   said optical fibers being connected to said container holder and arranged such that the sample in said container is excited for fluorescence from below said sample container held by said container holder, and said optical fibers receive fluorescent light emitted by the sample from below said sample container.

2. A fluorescence detecting apparatus according to claim 1 wherein said container holder is formed of a thermoconductive material.

3. A fluorescence detecting apparatus according to claim 1 wherein said container holder has a recess opening through a top surface thereof for receiving said sample container, said optical fibers extending through a bore opening through a bottom surface of said container holder and in communication with said recess whereby the optical fibers are exposed directly to said sample container.

4. A fluorescence detecting apparatus according to claim 3 wherein said recess in said container holder and said sample container are complementary in shape relative to one another.

5. A fluorescence detecting apparatus according to claim 1 wherein said container holder is formed of a thermoconductive material, and a heater coupled to said thermoconductive material for raising the temperature of the container holder and the sample carried by the sample container.

6. A fluorescence detecting apparatus according to claim 1 wherein said container holder is formed of a thermoconductive material, and means coupled to said thermoconductive material for lowering the temperature of the container holder and the sample carried by the sample container.

7. A fluorescence detecting apparatus comprising:
   a sealed sample container for holding a sample;
   a container holder for holding the sample container and means for varying the temperature of the sample in the sample container;
   a fluorescence detector for measuring the fluorescence from the sample;
   a light source for emitting an exciting light to excite the sample for fluorescence, and at least one light-interrupting shutter in the optical path of the exciting light used between the light source and the container holder to excite the sample for fluorescence;
   means for opening and closing the light-interrupting shutter in synchronization with the change in the temperature of the sample;
   said light source and said container holder, and said container holder and said fluorescence detector each being optically connected by optical fibers; and
   said optical fibers being connected to said container holder and arranged such that the sample in said container is excited for fluorescence from below said sample container held by said container holder, said optical fibers receiving fluorescent light emitted by the sample from below said sample container.

8. A fluorescence detecting apparatus according to claim 7 including means for opening and closing said light-interrupting shutter enabling synchronization with the measurement of the fluorescence from the sample.

9. A fluorescence detecting apparatus according to claim 7 wherein said container holder is formed of a thermoconductive material.

10. A fluorescence detecting apparatus according to claim 7 wherein said container holder has a recess opening through a top surface thereof for receiving said sample container, said optical fibers extending through a bore opening through a bottom surface of said container holder and in communication with said recess whereby the optical fibers are exposed directly to said sample container.

11. A fluorescence detecting apparatus according to claim 10 wherein said recess in said container holder and said sample container are complementary in shape relative to one another.

12. A fluorescence detecting apparatus according to claim 7 wherein said container holder is formed of a thermoconductive material, and a heater coupled to said thermoconductive material for raising the temperature of the container holder and the sample carried by the sample container.

13. A fluorescence detecting apparatus according to claim 7 wherein said container holder is formed of a thermoconductive material, and means coupled to said thermoconductive material for lowering the temperature of the container holder and the sample carried by the sample container.

* * * * *